United States Patent
Alsop et al.

(10) Patent No.: US 8,623,327 B2
(45) Date of Patent: Jan. 7, 2014

(54) IMAGING AGENTS FOR USE IN MAGNETIC RESONANCE BLOOD FLOW/PERFUSION IMAGING

(75) Inventors: David Alsop, Newton, MA (US); Elena Vinogradov, Boston, MA (US); Aaron K. Grant, Allston, MA (US); Robert E. Lenkinski, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 719 days.

(21) Appl. No.: 12/308,439

(22) PCT Filed: Jun. 19, 2007

(86) PCT No.: PCT/US2007/014310
§ 371 (c)(1),
(2), (4) Date: Oct. 27, 2010

(87) PCT Pub. No.: WO2007/149454
PCT Pub. Date: Dec. 27, 2007

(65) Prior Publication Data
US 2011/0040173 A1    Feb. 17, 2011

Related U.S. Application Data

(60) Provisional application No. 60/814,945, filed on Jun. 19, 2006.

(51) Int. Cl.
*A61B 5/055* (2006.01)

(52) U.S. Cl.
USPC .......................................... 424/9.3; 600/420

(58) Field of Classification Search
None
See application file for complete search history.

(56) References Cited

U.S. PATENT DOCUMENTS

| | | | |
|---|---|---|---|
| 6,453,188 | B1 | 9/2002 | Ardenkjaer-Larsen et al. |
| 6,574,495 | B1 | 6/2003 | Golman et al. |
| 2002/0058869 | A1 | 5/2002 | Axelsson et al. |

FOREIGN PATENT DOCUMENTS

| | | |
|---|---|---|
| WO | WO 99/24080 A1 | 5/1999 |
| WO | WO 99/35508 A1 | 7/1999 |
| WO | WO 02/23209 A2 | 3/2002 |
| WO | WO 2004/037296 A2 | 5/2004 |

OTHER PUBLICATIONS

Johansson E, Månsson S, et al. Cerebral perfusion assessment by bolus tracking using hyperpolarized 13C. 2004 Magn. Reson. Med. 51: 464-472.*
ChemSpider CSID:3315401. Available online at http://www.chemspider.com/Chemical-Structure.3315401.html. Accessed Feb. 24, 2013.*
Bernauer et al. Biotransformation of 12C- and 2-13C-labeled methyl tert-butyl ether, ethyl tert-butyl ether, and tert-butyl alcohol in rats: identification of metabolites in urine by 13C nuclear magnetic resonance and gas chromatography/mass spectrometry. 1998 Chem. Res. Toxicol. 11: 651-658.*
M. Plückthun, Ch. Bradtke, H. Dutz, R. Gehring, St. Goertz, J. Harmsen, P. Kingsberry, W. Meyer and G. Reicherz, "Polarization measurements of TEMPO-doped butanol targets," *Nuclear Instruments and Methods in Physics Research A*, 1997, pp. 133-136, vol. 400, No. 1.
F. P. Pruchnik, P. Smolenski and K. Wajda-Hermanowicz, "Rhodium(I) acetylacetonato complexes with functionalized phosphines," *Journal of Organometallic Chemistry*, 1998, pp. 63-69, No. 570.
International Search Report and Written Opinion for International Application No. PCT/US2007/014310 mailed Apr. 24, 2008.

* cited by examiner

*Primary Examiner* — Michael G Hartley
*Assistant Examiner* — Jennifer Lamberski
(74) *Attorney, Agent, or Firm* — Wolf, Greenfield & Sacks, P.C.

(57) ABSTRACT

In one aspect, a method of imaging blood flow in a region of interest of a subject using magnetic resonance imaging (MRI) is provided. The method includes introducing an imaging agent into the subject, the imaging agent including a compound having at least one hyperpolarized nucleus having a $T_1$ greater than 15 seconds and a water-octanol partition coefficient between −1 and 1, providing at least one excitation signal to the region of interest, the at least one excitation signal configured to invoke a nuclear magnetic resonance (NMR) effect at least in the introduced imaging agent, and detecting an NMR signal emitted by the region of interest in response to the at least one excitation signal. In another aspect, the imaging agent includes a carbon-13 enriched alcohol.

1 Claim, 5 Drawing Sheets

Fig. 5

IMAGING AGENTS FOR USE IN MAGNETIC RESONANCE BLOOD FLOW/PERFUSION IMAGING

RELATED APPLICATION

This application is a national stage application under 35 U.S.C. §371 of International Application Ser. No. PCT/US2007/014310, filed on Jun. 19, 2007, which claims priority under 35 U.S.C. 119(e) to U.S. Provisional Application Ser. No. 60/814945, entitled "CARBON-13 LABELED ALCOHOLS FOR USE IN BLOOD FLOW IMAGING WITH HYPERPOLARIZATION-ENHANCED MAGNETIC RESONANCE TECHNIQUES," filed on Jun. 19, 2006, which are herein incorporated by reference in their entireties.

FIELD OF THE INVENTION

The present invention relates to imaging agents for use in blood flow imaging procedures via magnetic resonance imaging (MRI).

BACKGROUND

Tracking blood flow into tissue ("perfusion") is an important tool for medical diagnosis and research. Tissues require blood in order to survive and function; a decrease in perfusion ("ischemia") is the principle mechanism in many of the major causes of mortality and morbidity, including myocardial ischemia, pulmonary embolism, and stroke. Perfusion also plays a critical role in cancer development. A tumor's capacity to augment blood flow by means of angiogenesis is a key limiting factor in cancer progression. Accordingly, diagnostic imaging techniques that can accurately and sensitively measure blood flow are needed for clinical and research studies.

Conventional methods for blood flow imaging have been proposed for a variety of imaging modalities including Positron Emission Tomography (PET), x-ray computed tomography (CT) and magnetic resonance imaging (MRI). PET methods include tracking radioisotope-labeled agents. These agents, added to the blood, emit positrons that are detectable by the PET scanning apparatus. In CT, iodated contrast agents are traditionally provided to the blood stream. The iodated contrast agents enhance the x-ray attenuation characteristics of the blood, increasing the contrast between the blood and surrounding tissue in the resulting CT image.

SUMMARY OF THE INVENTION

Some embodiments include a method of imaging blood flow in a region of interest of a subject using magnetic resonance imaging (MRI), the method comprising introducing an imaging agent into the subject, the imaging agent including a compound having at least one hyperpolarized nucleus having a $T_1$ greater than 15 seconds and a logarithm of the water-octanol partition coefficient between −1 and 1, providing at least one excitation signal to the region of interest, the at least one excitation signal configured to invoke a nuclear magnetic resonance (NMR) effect at least in the introduced imaging agent, and detecting an NMR signal emitted by the region of interest in response to the at least one excitation signal.

Some embodiments include a method of imaging blood flow in a region of interest of a subject using magnetic resonance imaging (MRI), the method comprising introducing an imaging agent into the subject, the imaging agent including a carbon-13 enriched alcohol, providing at least one excitation signal to the region of interest, the at least one excitation signal configured to invoke a nuclear magnetic resonance (NMR) effect at least in the introduced imaging agent, and detecting an NMR signal emitted by the region of interest in response to the at least one excitation signal.

DETAILED DESCRIPTION

Despite the need for obtaining quality images of blood perfusion in various portions of the body, conventional methods of blood flow imaging often have drawbacks. Radioisotope-labeled tracking agents used in PET scanning pose significant safety hazards and typically offer only limited resolution and sensitivity. Iodinated contrast agents employed in CT scanning are typically incapable of penetrating the blood-brain barrier and therefore may not be suitable for blood flow imaging of brain tissue or suspected tumors. Moreover, although the rate of iodinated contrast arrival into other tissues can depend on perfusion, the rate that the compounds leave the blood stream is strongly determined by the natural permeability of capillaries. The combination of both perfusion and permeability makes it difficult to obtain reliable results from CT blood flow imaging studies. Background sources of signal may complicate the analysis as well. In particular, high background signals may limit the true signal-to-noise ratio (SNR) of the imaging process because motion and other artifacts that are typically proportional to the background signal intensity can dominate the noise of the measurement.

Magnetic resonance imaging (MRI) is a technique frequently used for blood flow/perfusion imaging. MRI is based on detecting nuclear magnetic resonance (NMR) signals, which are electromagnetic waves emitted by atomic nuclei in response to state changes resulting from applied electromagnetic fields. In particular, magnetic resonance (MR) techniques involve detecting NMR signals produced upon the re-alignment or relaxation of the nuclear spin of atoms in the body (e.g., in blood, tissue, etc.). MRI operates by manipulating the spin characteristics of molecules and includes aligning the spins of nuclei with an axial magnetic field $B_0$, and then perturbing the magnetic field in a targeted region with one or more radio frequency (RF) magnetic fields $B_1$.

The NMR phenomenon results from exciting nuclei by generating RF signals $B_1$ at the Larmor frequency and applying them to a region of interest. The Larmor frequency is related to the rate at which nuclear spins precess about an axis at a given strength of the axial magnetic field $B_0$. When placed in magnetic field $B_0$, the spin of atomic nuclei align in one of two configurations: 1) a low energy configuration in which spins align in the opposite direction of the magnetic field (i.e., anti-align); and 2) a high energy configuration in which spins align in the same direction as the magnetic field, with more atoms aligning with the magnetic field than anti-aligning at equilibrium (i.e., the state of the nuclear spins in the presence of applied magnetic field $B_0$ alone).

An applied RF magnetic field $B_1$ causes the nuclear spins to change orientation, and causes some nuclei to achieve a higher energy state. When the RF signal $B_1$ subsides, the nuclear spins realign with the axial magnetic field $B_0$. Those nuclei that achieved the higher energy state upon excitation, return to the lower energy state by releasing electromagnetic energy. The released electromagnetic energy may be detected as NMR signals and used to form one or more images representative of the tissue type in the region of interest. Thus, the population difference between the number of aligned and anti-aligned nuclei is related to the to strength of the NMR signal released upon relaxation. The NMR signals may be detected using one or more RF coils sensitive to electromagnetic changes caused by the NMR signals. Similarly; the NMR phenomenon may be invoked in part, using RF coils that generate an excitation RF pulse sequence. Numerous pulse sequences suitable for obtaining NMR signals are known, and will not be discussed in detail herein.

Conventional MR techniques for blood flow imaging may be unsuitable for a number of reasons. Many conventional MRI contrast agents consist of large molecules, or chelates that are not capable of flowing into most tissues. As a result, these contrast agents may be of limited or no use in certain parts of the body. Attempts at using smaller size molecules as imaging agents that may effectively flow into a wider range of tissues have been frustrated by either toxicity of the agents or the insufficient signal intensity resulting from the agents, making their use generally impractical. Another drawback of conventional MRI contrast agents include relatively short spin-lattice relaxation times ($T_1$), which limit the time the agent has to penetrate a region of interest and accumulate so as to generate sufficient signal strength to measure tissue perfusion.

Hyperpolarization techniques offer a means to create useful signals even with smaller agents, but existing efforts have not yielded hyperpolarized substances that are practical to employ as general perfusion agents. Hyperpolarization increases SNR by increasing the population difference between nuclei that attain the higher energy state and lower energy state in equilibrium. As discussed above, the population difference is proportional to the NMR signal strength and increasing the population difference has the effect of increasing emitted NMR signal strength.

An early technique using hyperpolarization to facilitate blood flow imaging in MRI relied on the laser excitation of certain noble gases (e.g., either xenon or the 3He isotope of helium). 3He is not soluble in blood and accordingly may not be suitable for tracking perfusion. Xenon is soluble in blood, but is not satisfactory for several reasons. First, the gas interacts with lipids in tissues, thereby causing large shifts in frequency and shortening $T_1$, thus reducing the time it takes nuclei to reequilibrate after hyperpolarization. Relaxation times are typically less than 10 seconds in blood, and as little as 2 seconds in tissue. Accordingly, the $T_1$ may be too short to facilitate imaging blood perfusion.

Because the maximum concentration of xenon in blood is quite small (e.g., to avoid to anesthetic effects such as unconsciousness), it takes a relatively long time for an adequate concentration of the gas to accumulate in tissue (e.g., more than one minute). Therefore, hyperpolarized xenon may not be preserved long enough for a sufficient amount of the agent to reach the area of interest and accumulate there. In addition, the concentration of xenon necessary for the MRI procedure is relatively high (e.g., typically more than fifty percent of the concentration sufficient to cause patients to lose consciousness). Yet another concern arises from the fact that xenon's interaction with lipids, as in red blood cells, may slow the rate of release into the tissue of interest, essentially making xenon a diffusion limited tracer at high flow.

Applicant has appreciated that the problems encountered with xenon evidence a need for agents that have a relatively long $T_1$, generally low toxicity (e.g., such that concentrations in the 1 to 10 mM range in the brain and other tissues are acceptable), and an ability to pass readily into lipid membranes in the walls of blood vessels and cells without excessive interaction with the lipids in the membranes themselves. For example, Applicant has appreciated that imaging agents that are both soluble in water and lipids may facilitate generally free diffusion of the agents across lipid membranes. In addition, the background level of such tracers in the body should be minimal to avoid reducing the SNR of the signal.

New opportunities for the creation of agents having one or more of the above beneficial characteristics have arisen from the development of several "ex vivo" methods of hyperpolarizing carbon-13 enriched compounds and then injecting them into the sample of interest. One such technique, referred to as dynamic nuclear polarization ("DNP"), relies on the freezing of the imaging agent in a glass state, irradiating the material with microwaves, and then rapidly warming the agent DNP has been used to increase the signal from carbon-13 enriched liquids by several orders of magnitude. A more detailed discussion of various DNP techniques are described in U.S. Pat. No. 6,453,188, Which is herein incorporated by reference in its entirety. A second technique, referred to as para-hydrogen induced polarization ("PHIP"), involves the reaction of para-hydrogen ($H_2$ in the singlet spin state) with an imaging agent precursor containing carbon-13 to produce a hydrogenated imaging agent. A more detailed discussion of PHIP techniques are discussed in U.S. Pat. No. 6,574,495, which is herein incorporated by reference in its entirety.

Applicant has appreciated that the use of a certain class of imaging agents may remedy one or more of the above described problems associated with conventional imaging agents. In particular, Applicant has identified a class of imaging agents for use in MRI imaging as a blood flow tracer that can be hyperpolarized and injected or inhaled. Certain molecules in the class of imaging agents are generally soluble in both water and lipids, facilitating perfusion imaging in a wide range of tissues including, but not limited to, brain tissues which have been difficult to image with respect to blood flow (due in part to the blood brain barrier). In addition, some compounds according to the present invention have relatively long $T_1$ times suitable for blood flow imaging.

In some embodiments according to the present invention, carbon-13 enriched alcohols are used as an imaging agent to obtain one or more MRI images of blood perfusion. Carbon-13 enriched alcohols represent an effective class of compounds to hyperpolarize via DNP or PHIP and in turn use for MRI perfusion studies. Alcohols are highly soluble in both water and lipids. In particular, they can cross the blood-brain barrier as well as cellular membranes, fostering high concentrations in tissue and ensuring that little or none of the magnetic resonance signal will be attributable to background concentrations. The cellular permeability also increases the mean transit time in the tissue, thereby decreasing the required temporal resolution for imaging and allowing for slower injection of the tracking agent.

Carbon-13 enriched alcohols may offer several practical advantages as well. Alcohols are relatively nontoxic, and their bio-distribution has been extensively studied. Accordingly, the effects of alcohol in the body are well known and relatively safe at contemplated levels. In non-enriched tissues, moreover, the background signal of carbon 13 is almost zero, thus reducing noise and increasing SNR. Carbon-13 enrichment of alcohols is a known and relatively standard procedure, and many basic alcohols are available in enriched form as catalog items, making such agents readily available to the medical community without requiring customized production.

Figure 1A:
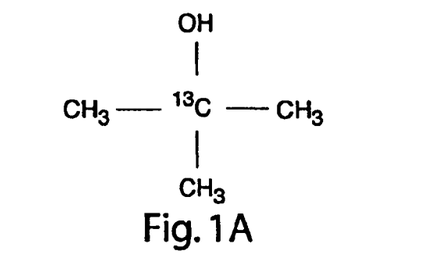
FIGS. 1A-1D illustrate various configurations of a text-butyl alcohol (t-butanol) imaging agent, in accordance with some embodiments of the present invention.
Figure 1B:
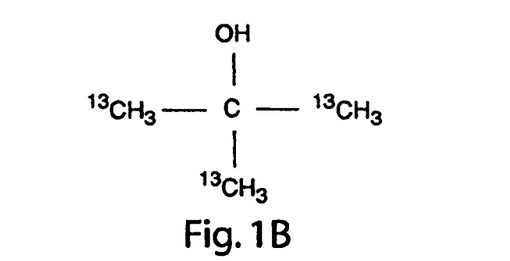

Applicant has identified a number of compounds that can be used as imaging agents that facilitate obtaining images of blood flow/perfusion. FIGS. 1A-1D illustrate various configurations of a tert-butyl alcohol (t-butanol) molecule that may be used as a contrast agent to image blood flow, in accordance with some embodiments of the present invention. FIG. 1A illustrates the t-butanol molecule enriched with carbon-13 at the central tertiary carbon. This configuration may result in a particularly long $T_1$ due, in part, to the four bonds with non-magnetic nuclei shielding the central carbon-13 atom from the magnetic moments of the outlying proton magnetic moments. Alternatively, the three carbons in the outlying methyl groups may be enriched with carbon 13 as illustrated in FIG. 1B. Other configurations of enriching t-butanol with carbon-13 may be used as well (e.g., combinations of enriching the outlying and central carbons), as the aspects of the invention are not limited in this respect. Any of the above described molecules may be a suitable candidate for DNP to hyperpolarize the molecules to increase NMR signal strength.

Figure 1C:
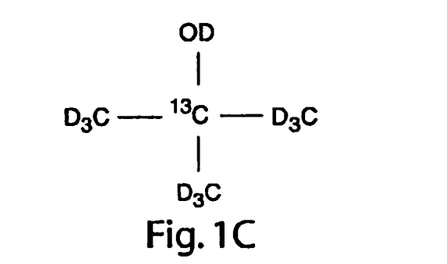
Figure 1D:
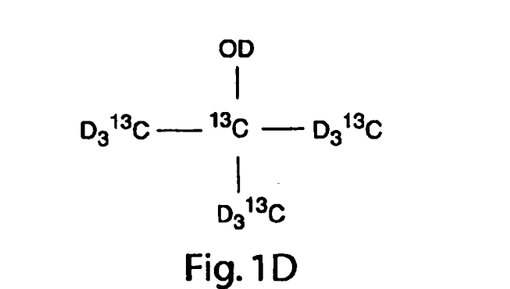
Figure 2A:
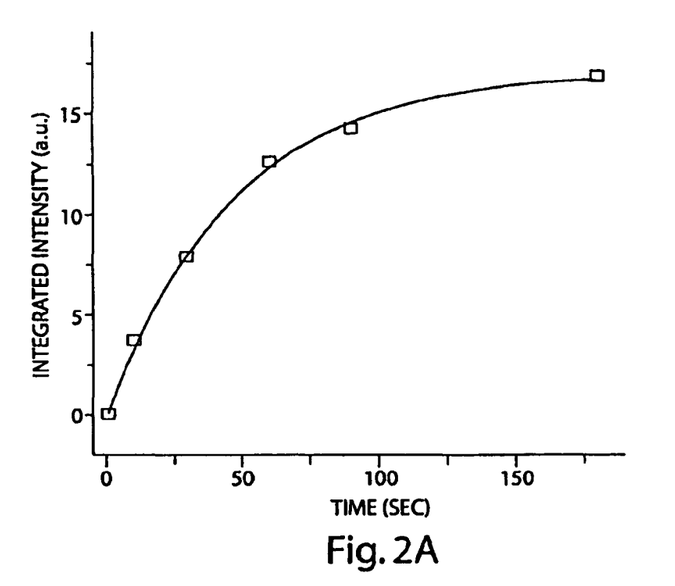
FIGS. 2A and 2B are graphs illustrating the integrated signal for a single saturation recovery experiment obtained using deuterated t-butanol with carbon-13 enhancement of the central carbon, in accordance with some embodiments of the present invention.
Figure 2B:
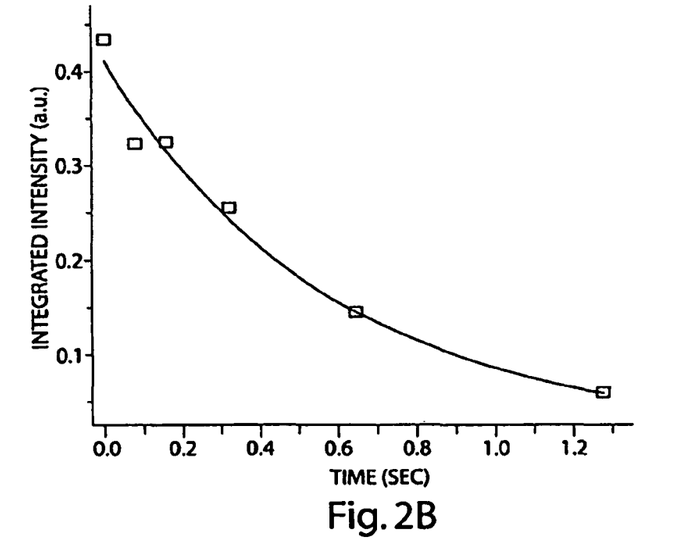

The $T_1$ of the t-butanol molecule can be further increased by replacing the outlying hydrogen atoms with deuterium as illustrated in FIG. 1C. It has been determined that a deuterated sample of t-butanol with carbon-13 enrichment of the tertiary carbon has a $T_1$ in excess of 20 seconds at 400 Mhz when measured in water with oxygen present. Although the $T_1$ of deuterated t-butanol with carbon-13 enrichment of the methyl groups (e.g., as illustrated in FIG. 1D) is shorter, this species may be advantageous because of the enriched signal strength resulting from the three carbons on each molecule. The median value of $T_1$ at 400 Mhz, 9.6 T, for deuterated t-butanol with carbon-13 enhancement of the central carbon was 64±20 sec, and $T_1$ for deuterated t-butanol with carbon-13 enhancement of the methyl carbons was 26±5 sec. FIGS. 2A and 2B are graphs illustrating the integrated signal for a single saturated recovery experiment obtained using deuterated t-butanol with the carbon-13 enhancement of the central carbon, in which $T_1$=46±4 and $T_2$=0.6±0.02. The relatively long $T_2$ may yield further SNR enhancements.

As discussed above, carbon-13 enriched alcohols may be hyperpolarized to increase NMR signal strength. For example, one procedure for DNP of t-butanol includes mixing the liquid alcohol with a free radical such as 2,2,6,6-tetramethyl-piperidine-1-oxyl, then rapidly freezing the mixture by dripping through cold gas. The agent is hyperpolarized by subjecting it to microwave irradiation at low temperature, then prepared for injection by rapid warming, for example, using the water method disclosed in U.S. Patent Publication No. 2002/0058869, which is herein incorporated by reference in its entirety. Although the free radical may be filtered out, its toxicity at concentrations contemplated for perfusion imaging is not high. Further detail describing DNP of deuterated butanol are described in Nuclear Instruments and Methods in Physics Research A 400:133-136 (1997), which is herein incorporated by reference in its entirety. DNP of t-butanol or deuterated butanol may be performed according to other methods, as the aspects of the invention are not limited in this respect.

Figure 3A:
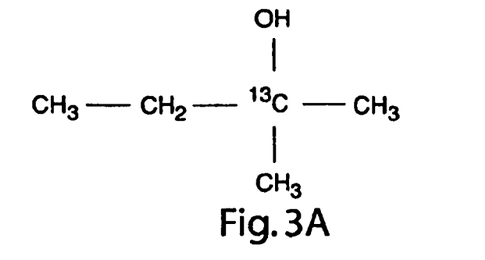
FIGS. 3A-3D illustrate various configurations of a 2-methyl-2-butanol imaging agent, in accordance with some embodiments of the present invention.
Figure 3B:
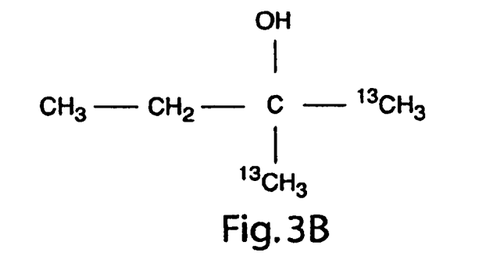

FIGS. 3A-3B illustrate various configurations of a 2-methyl-2-butanol molecule suitable as an imaging agent, in accordance with some embodiments of the present invention.

Figure 3C:
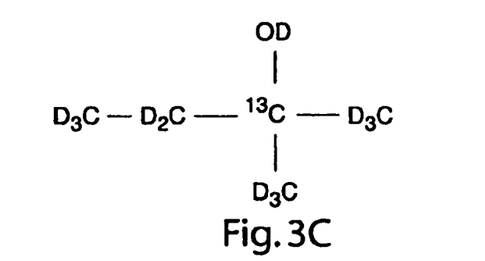
Figure 3D:
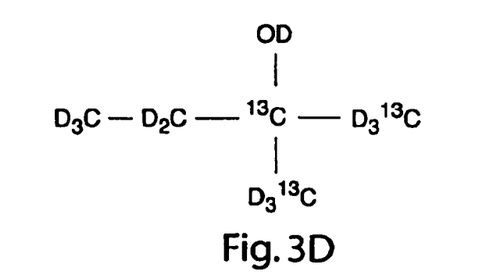

FIG. 3A illustrates 2-methyl-2-butanol enriched with carbon 13 at the central tertiary carbon, however, the two adjacent methyl groups may be enriched with carbon 13, either alone or in combination with the central tertiary carbon. For example, FIG. 3B illustrate the two methyl groups enriched with carbon-13 in place of the central carbon. As with t-butanol, $T_1$ of the molecule can be further increased by replacing the outlying hydrogen atoms with deuterium as illustrated in FIGS. 3C and 3D. Any of the above described molecules may be suitable candidates for hyperpolarization using PHIP, which can be readily synthesized by the hydrogenation of dimethyl vinyl carbinol in the presence of a rhodium catalyst, as discussed in J. Organomet. Chem. 570:63-69 (1998), which is herein incorporated by reference in its entirety.

Figure 4:
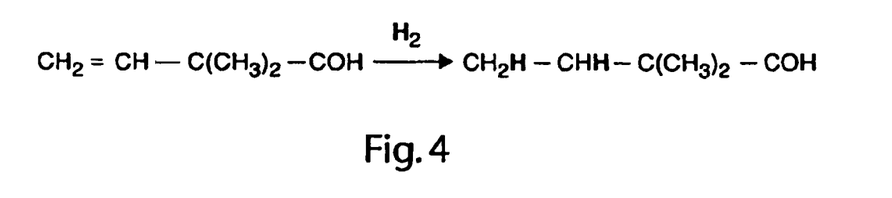
FIG. 4 illustrates a scheme for preparing hyperpolarized 2-methyl-2-butanol by means of para-hydrogen induced polarization, in accordance with some embodiments of the present invention.

FIG. 4 illustrates a scheme for preparing hyperpolarized 2-methyl-2-butanol by means of para-hydrogen induced polarization. In particular, 2-methyl-3-buten-2-ol (dimethyl vinyl carbinol) is hydrogenated with para-hydrogen to form the hyperpolarized 2-methyl-2-butanol. While dimethyl vinyl carbinol provides a suitable precursor, other precursors may be used, as the aspects of the invention are not limited in this respect. Following the reaction of the carbon 13 enriched substrate with para-hydrogen gas in the presence of the rhodium catalyst, the agent may be filtered if necessary to remove the catalyst and any remaining, non-hydrogenated substrate.

Hyperpolarized t-butanol and 2-methyl-2-butanol may offer several particular advantages as an imaging agent. As discussed above, the hyperpolarized molecules have relatively long relaxation times that may be long enough for transfer, injection, distribution and imaging. In addition, both molecules may be freely diffusible across lipid membranes due, in part, to the property that the molecules are soluble in both water and lipids. A common measure of the solubility of a compound or molecule is the water-octanol partition coefficient. The water-octanol coefficient is a measure of the differential solubility of the compound between the two solvents. While other solvents may be used, water and octanol are useful to measure how hydrophilic (e.g., the extent of the solubility of the compound in water) and how hydrophobic (e.g., the extent of the solubility of the compound in octanol) the compound is. The solubility in octanol is an indicator of how lipid soluble the compound is, and may therefore be a useful measure of how freely a compound diffuses across, for example, the blood brain barrier, or other lipid membranes. The water-octanol partition coefficient may be computed as:

$$\log\left(\frac{Solute_{octanol}}{Solute_{water}}\right). \qquad (1)$$

Determining the water-octanol partition coefficient for a molecule is well known and will not be discussed in detail herein. Molecules that are soluble in both water and lipids such that they are relatively diffusible across lipid membranes typically have a water-octanol partition coefficient in a range between −1 and 1. Hyperpolarized t-butanol and 2-methyl-2-butanol are relatively small and have log water-octanol partition coefficients close to zero, indicating that they have almost equal affinity for water and lipids. The alcohols therefore are highly membrane permeable while remaining water soluble, allowing for penetration of the blood-brain barrier and tissue cell membranes. The free permeability also increases the concentration of the agents in the tissue and lengthens the outflow time constant by up to an order of magnitude relative to agents that do not penetrate cell membranes.

In addition, the metabolism and toxicity of t-butanol has been extensively studied because it is a breakdown product of the fuel additive MBTE. T-butanol is not processed by the alcohol dehydrogenase enzyme. Instead, the majority of the agent is removed more slowly, likely through the lungs and urine in original form or relatively safe metabolites. Conjugation with glucuronic acid occurs, as does oxidation to 2-methyl-1,2-propanediol,2-hydroxyisobutyrate, and potentially acetone and formaldehyde, but in low concentrations.

There may also be particular advantages to the use of 2-methyl-2-butanol or other hyperpolarized alcohols produced by reaction with para-hydrogen. The PHIP technique can be performed by a number of methods (including field cycling) either before or after incorporation into the delivery mechanism of choice (e.g., a syringe or power injector), thus facilitating relatively fast administration following hyperpolarization to minimize $T_1$ decay. In addition, the does not necessitate the use of cryogenic apparatus to the same extent that DNP techniques demand, nor does PHIP require the introduction of a free radical agent.

T-butanol and 2-methyl-2-butanol are only representative examples of the present invention, which is not limited in its application to the embodiments described herein. In particular, numerous other carbon-13 enriched alcohols may offer many of the same qualities including, but not limited to, a high affinity for both water and lipids that make t-butanol and 2-methyl-2-butanol valuable agents for blood flow imaging. Many similar alcohols have configurations that would allow their use in hyperpolarization techniques such as DNP or PHP. Carbon-13 enriched ethanol, for example, may be an attractive imaging agent because of its simplicity and the extensive research regarding the toxic effects of ethanol. The agent's relatively short $T_1$ can be lengthened by replacing the hydrogen atoms with deuterons. Carbon-13 enriched butanol is another simple alcohol whose use as an MRI perfusion agent is encompassed in the present invention. While carbon-13 provides a nuclei with a suitably long $T_1$, molecules comprised of different nuclei having relatively long $T_1$ (e.g., $T_1$ greater than approximately 15 seconds) may be used as well, such as molecules containing nitrogen-15, as the aspects of the invention are not limited for use with molecules enriched with carbon-13.

Figure 5:
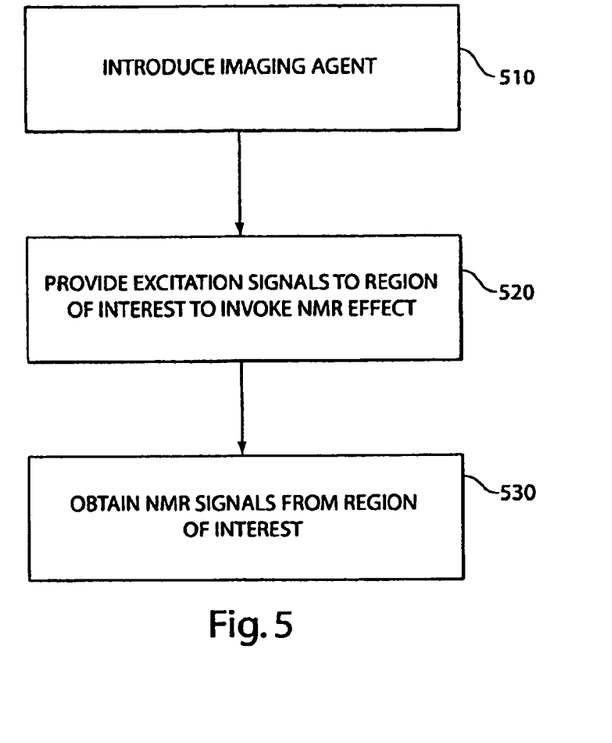
FIG. 5 is a flow chart illustrating a method of using an imaging agent to facilitate imaging blood flow/perfusion, in accordance with some embodiments of the present invention.

FIG. 5 illustrates a method of using an imaging agent to facilitate imaging blood flow/perfusion, in accordance with some embodiments of the present invention. In act 510, the imaging agent is introduced to the subject being imaged. The term "introduce" refers herein to any mechanism used to admit or otherwise deliver the imaging agent into the system of the subject. For example, an imaging agent may be injected into the subject, for example, into a vein or artery of the subject. Alternatively, the imaging agent may be introduced via inhalation of the imaging agent by the subject. Other mechanisms for introducing the imaging agent, such as orally or other methods of ingestion, may be used, as the aspects of the invention are not limited in this respect. The imaging agent may be a carbon-13 enriched alcohol (e.g., any of the variations of molecules illustrated in FIGS. 1A-1D or FIGS. 3A-3B), or a molecule that has a relatively long $T_1$ and is generally diffusible across lipid membranes, as the aspects of the invention are not limited in this respect.

In acts 520 and 530 the subject may undergo MRI imaging. For example, excitation signals adapted to induce the NMR effect may be provided to a region of interest on the subject (e.g., a region for which blood flow/perfusion imaging is desired), and the resulting NMR signals emitted from the region of interest detected. Imaging of the region of interest can be performed using any MRI methods for acquisition of one or more images at particular time intervals after introducing the imaging agent to the subject and/or using any MRI scanning equipment. Modeling of the time dependence and its relationship to the obtained NMR signal may be employed to calculate blood flow. Other methods for measuring blood flow/perfusion from the MR data may used as well, as the aspects of the invention are not limited in this respect.

The present invention may also facilitate the expansion of magnetic resonance screening using devices that are smaller, less expensive, and/or more specialized than existing MRI equipment. Hyperpolarization techniques can produce large signals even at lower field strengths. One embodiment of the present invention is therefore the use of carbon 13 enriched alcohols for blood flow imaging in conjunction with specialized screening devices, including but not limited to mammography apparatus, that rely on weaker magnetic fields than conventional MRI units typically generate.

Various aspects of the present invention may be used alone, in combination, or in a variety of arrangements not specifically discussed in the embodiments described in the foregoing. In particular, the compounds described above are merely exemplary and other compounds may be used, as the aspects of the invention are not limited in this respect. Accordingly, the foregoing description and drawings are by way of example only. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Various aspects of the present invention may be implemented in connection with any type MR imaging equipment of any configuration. In particular, subjects to which any one or combination of imaging agents described herein may be imaged using any imaging equipment capable of generating excitation signals adapted to invoke an NMR effect and capable of detecting emitted NMR signals. No limitations are placed on the implementation and/or configuration of the imaging equipment. Similarly, any type of blood flow/perfusion imaging method may be used to obtain images of blood flow/perfusion in a subject to which an imaging agent has been introduced. In addition, any type of mechanism may be used to introduce a selected imaging agent, as the aspects of the invention are not limited for use with any particular method of introduction.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A method of obtaining nuclear magnetic resonance information for use in imaging blood flow in a region of interest of a subject using magnetic resonance imaging (MRI), the method comprising:
   introducing an imaging agent into the subject, the imaging agent comprising a compound having at least one hyperpolarized nucleus having a $T_1$ greater than 15 seconds and a log water-octanol partition coefficient between and including −1 and 1, wherein the compound is capable of substantial penetration of the blood-brain barrier, and wherein the compound is carbon-13 enriched tert-butyl alcohol (t-butanol) or carbon-13 enriched 2-methyl-2-butanol;
   providing at least one excitation signal to the region of interest, the at least one excitation signal configured to invoke a nuclear magnetic resonance (NMR) effect at least in the introduced imaging agent; and
   detecting an NMR signal emitted by the region of interest in response to the at least one excitation signal.

* * * * *